(12) United States Patent
Suvorov et al.

(10) Patent No.: US 9,345,757 B2
(45) Date of Patent: May 24, 2016

(54) **CHIMERIC PROTEIN VACCINE AGAINST PNEUMONIA CAUSED BY *STREPTOCOCCUS PNEUMONIAE***

(71) Applicant: Epitope Limited, St. Petersburg (RU)

(72) Inventors: Aleksandr Nikolaevich Suvorov, St. Petersburg (RU); Ilya Vladimirovich Dukhovlinov, St. Petersburg (RU); Anton Iosifovich Orlov, St. Petersburg (RU); Evgenii Jakovlevich Baiguzin, St. Petersburg (RU)

(73) Assignee: EPITOPE LIMITED, St. Petersburg (RU)

( * ) Notice: Subject to any disclaimer, the term of this patent is extended or adjusted under 35 U.S.C. 154(b) by 0 days.

(21) Appl. No.: 14/579,279

(22) Filed: Dec. 22, 2014

(65) Prior Publication Data

US 2015/0174230 A1 Jun. 25, 2015

Related U.S. Application Data

(63) Continuation of application No. PCT/RU2013/000525, filed on Jun. 21, 2013.

(30) Foreign Application Priority Data

Jun. 22, 2012 (RU) .................. 2012126328

(51) Int. Cl.
*A61K 39/09* (2006.01)
*C07K 14/315* (2006.01)
*A61K 39/00* (2006.01)

(52) U.S. Cl.
CPC ........... *A61K 39/092* (2013.01); *C07K 14/3156* (2013.01); *A61K 2039/6068* (2013.01)

(58) Field of Classification Search
None
See application file for complete search history.

(56) References Cited

U.S. PATENT DOCUMENTS

| | | |
|---|---|---|
| 2007/0082003 A1 | 4/2007 | Leenhouts et al. |
| 2008/0305123 A1 | 12/2008 | Ades et al. |
| 2010/0221288 A1 | 9/2010 | Zagursky et al. |
| 2010/0260790 A1 | 10/2010 | Meinke et al. |
| 2010/0266625 A1 | 10/2010 | Tai et al. |
| 2010/0278740 A1 | 11/2010 | Gilbert et al. |
| 2011/0287052 A1 | 11/2011 | Curtiss, III et al. |
| 2012/0135037 A1 | 5/2012 | Mizel et al. |

FOREIGN PATENT DOCUMENTS

| | | |
|---|---|---|
| WO | 2004102199 A2 | 11/2004 |
| WO | 2010120921 A1 | 10/2010 |

OTHER PUBLICATIONS

Greenspan et al (Nature Biotechnology, 1999, 7:936-937).*
Lu Y-J, et al. "A bivalent vaccine to protect against *Streptococcus pneumoniae* and *Salmonella typhi*", Vaccine (2012), 8 pages.
Arêas, et al.; "Expression and characterization of cholera toxin B-pneumococcal surface adhesin A fusion protein in *Escherichia coli*: ability of CTB-PsaA to induce humoral immune response in mice", Biochemical and Biophysical Research Communications 321 (2004) 192-196.
Wu, et al., "Intranasal Immunization of Mice with PspA (Pneumococcal Surface Protein A) Can Prevent Intranasal Carriage, Pulmonary Infection, and Sepsis with *Streptococcus pneumoniae*", The Journal of Infectious Diseases 1997;175:839-46.
International Search Report Application No. PCT/RU2013/000525 Completed: Sep. 4, 2013, Mailing Date: Oct. 31, 2013 1 page.
Schuerman, et al., "Prevention of otitis media: Now a reality?", Vaccine 27 (2009) 5748-5754.
Segal, et al., "Vaccines against bacterial meningitis", British Medical Bulletin 2004; 72: 65-81.

* cited by examiner

*Primary Examiner* — Padma V Baskar
(74) *Attorney, Agent, or Firm* — The Roy Gross Law Firm, LLC; Roy Gross

(57) ABSTRACT

A vaccine comprising a chimeric protein set forth as SEQ ID NO: 1 containing immunogenic epitopes of conservative *Streptococcus pneumoniae* proteins PspA, Spr1895, PsaA, as well as flagellin components, connected via flexible links, wherein the flagellin components function as adjuvant.

1 Claim, 2 Drawing Sheets

SEQUENCE LISTING

<160> NUMBER OF SEQ ID NOS: 1

<210> SEQ ID NO 1
<211> LENGTH: 536
<212> TYPE: PRT
<213> ORGANISM: Artificial Sequence
<220> FEATURE:
<221> NAME/KEY: DOMAIN
<222> LOCATION: (1)...(169)
<223> OTHER INFORMATION: FliC domain 1, from 1 to 169 amino acids of

```
        gb|AAB33952.1|
<220> FEATURE:
<221> NAME/KEY: DOMAIN
<222> LOCATION: (182)...(276)
<223> OTHER INFORMATION: FliC domain 2, from 311 to 405 amino acids of
        gb|AAB33952.1|
<220> FEATURE:
<221> NAME/KEY: DOMAIN
<222> LOCATION: (281)...(386)
<223> OTHER INFORMATION: PspA epitope, from 160 to 262 amino acids of
        gb|EHD89266.1|
<220> FEATURE:
<221> NAME/KEY: DOMAIN
<222> LOCATION: (391)...(458)
<223> OTHER INFORMATION: Spr1895 epitope, from 94 to 161 amino acids of
        ref|ZP_01836139.1|
<220> FEATURE:
<221> NAME/KEY: DOMAIN
<222> LOCATION: from 466 to 536 amino acids
<223> OTHER INFORMATION: PsaA epitope, from 238 to 309 amino acids of
        gb|AAF70667.1|

<400> SEQUENCE: 1

Ala Gln Val Ile Asn Thr Asn Ser Leu Ser Leu Leu Thr Gln Asn Asn
1               5                   10                  15

Leu Asn Lys Ser Gln Ser Ala Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ala Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ala Val
                85                  90                  95

Gln Ser Ala Asn Ser Thr Asn Ser Gln Ser Asp Leu Asp Ser Ile Gln
            100                 105                 110

Ala Glu Ile Thr Gln Arg Leu Asn Glu Ile Asp Arg Val Ser Gly Gln
        115                 120                 125

Thr Gln Phe Asn Gly Val Lys Val Leu Ala Gln Asp Asn Thr Leu Thr
    130                 135                 140

Ile Gln Val Gly Ala Asn Asp Gly Glu Thr Ile Asp Ile Asp Leu Lys
145                 150                 155                 160

Gln Ile Asn Ser Gln Thr Leu Gly Leu Gly Gly Ser Gly Gly Gly
                165                 170                 175

Ser Gly Gly Gly Ser Ala Ala Thr Thr Thr Glu Asn Pro Leu Gln Lys
            180                 185                 190

Ile Asp Ala Ala Leu Ala Gln Val Asp Thr Leu Arg Ser Asp Leu Gly
        195                 200                 205

Ala Val Gln Asn Arg Phe Asn Ser Ala Ile Thr Asn Leu Gly Asn Thr
    210                 215                 220

Val Asn Asn Leu Thr Ser Ala Arg Ser Arg Ile Glu Asp Ser Asp Tyr
225                 230                 235                 240

Ala Thr Glu Val Ser Asn Met Ser Arg Ala Gln Ile Leu Gln Gln Ala
                245                 250                 255

Gly Thr Ser Val Leu Ala Gln Ala Asn Gln Val Pro Gln Asn Val Leu
            260                 265                 270

Ser Leu Leu Arg Gly Gly Gly Ser Ala Met Ala Asp Leu Lys Lys Ala
        275                 280                 285

Val Asn Glu Pro Glu Lys Pro Ala Glu Glu Glu Pro Glu Asn Pro Ala
```

-continued

```
            290                 295                 300
Pro Ala Pro Lys Pro Ala Pro Ala Pro Gln Pro Glu Lys Pro Ala Pro
305                 310                 315                 320

Ala Pro Ala Pro Lys Pro Glu Lys Ser Ala Asp Gln Gln Ala Glu Glu
                325                 330                 335

Asp Tyr Ala Arg Arg Ser Glu Glu Tyr Asn Arg Leu Thr Gln Gln
                340                 345                 350

Gln Pro Pro Lys Ala Glu Lys Pro Ala Pro Ala Pro Val Pro Lys Pro
            355                 360                 365

Glu Gln Pro Ala Pro Ala Pro Lys Thr Gly Trp Gly Gln Glu Asn Gly
        370                 375                 380

Met Trp Gly Gly Gly Ser Asn Glu Ala Glu Glu Val Thr Glu Val Glu
385                 390                 395                 400

Ile Gln Thr Pro Gln Ala Asp Ser Ser Glu Glu Val Thr Thr Ala Thr
                405                 410                 415

Ala Asp Leu Thr Thr Asn Gln Val Thr Val Asp Asp Gln Thr Val Gln
                420                 425                 430

Val Ala Asp Leu Ser Gln Pro Ile Ala Glu Ala Pro Lys Glu Val Ala
            435                 440                 445

Ser Ser Ser Glu Val Thr Lys Thr Val Ile Gly Gly Gly Gly Ser Ser
        450                 455                 460

Ser Leu Val Glu Lys Leu Arg Gln Thr Lys Thr Pro Ser Leu Phe Val
465                 470                 475                 480

Glu Ser Ser Val Asp Asp Arg Pro Met Lys Thr Val Ser Gln Asp Thr
                485                 490                 495

Asn Ile Pro Ile Tyr Ala Gln Ile Phe Thr Asp Ser Ile Ala Glu Gln
                500                 505                 510

Gly Lys Glu Gly Asp Ser Tyr Tyr Asn Met Met Lys Tyr Asn Leu Asp
            515                 520                 525

Lys Ile Ala Glu Gly Leu Ala Lys
530                 535
```

CHIMERIC PROTEIN VACCINE AGAINST PNEUMONIA CAUSED BY *STREPTOCOCCUS PNEUMONIAE*

FIELD OF THE INVENTION

The present invention relates to medicine, pharmacology, biotechnology and can be used for both prophylaxis and treatment of pneumonia caused by pneumococci (*Streptococcus pneumoniae* (*S. pneumoniae*)).

BACKGROUND OF THE INVENTION

The term "hybrid (or chimeric) protein" refers to a protein obtained as a result of the expression of a recombinant DNA molecule, in which coding arrays of several different genes are bound to one reading frame.

Pneumonia (syn. pulmonic fever) is a common disease of both adults and children and demands conscientious diagnostics and treatment. According to medical statistics, more than one million Russians contract pneumonia annually, and for 5% of patients this disease ends fatally (http://www.who.int/mediacentre/factsheets/fs331/ru/index.html).

The term "pneumonia" refers to a wide range of diseases, each of which possesses its own etiology, pathogenesis, clinical presentation, X-ray characteristics, laboratory data, and specific therapy, can progress as an independent disease or as a sequel of other diseases.

Pneumonia is an inflammatory condition of the human respiratory system. Among the causative agents of pneumonia there are viruses and fungi, but most commonly this disease is caused by bacteria. The most common pathogen that causes bacterial pneumonia is pneumococcus (*S. pneumoniae*). Examination of pharyngeal microflora has revealed that 5-25% of healthy people are carriers of pneumococcus.

Pneumococci are characterized by a thick polysaccharide capsule that protects the germ against opsonization and subsequent phagocytosis. As the consequence of the fact that the capsule turns to be the main superficial structure of the pneumococci recognized by an immune system, capsule polysaccharide is characterized by the highest variability. Until present, 91 different capsule types of pneumococci have been detected; however, the majority (more than 90%) of invasive pneumococcal diseases is caused by 23 mostly widespread serovars. A high number of immunological variants of capsule polysaccharide turns to be the factor to complicate producing of effective polysaccharide vaccines.

Every human can contract pneumococcal infection, but several risk groups exist, which are susceptible to this disease with higher expectancy. Those are persons 65 years old and older, small infants, persons with certain health disorders, persons with weakened immune system, smokers.

In many cases pneumococcal infection hardly responds to treatment, whereas numerous circulating epidemic pneumococcal stains develop multiple antibiotic resistances. For preventive purposes vaccines are used. According to WHO (World Health Organization) and Russian Respiratory Society, "Vaccination is the only possibility to prevent pneumococcal inflectional pathway". Currently, FDA (Food and Drug Administration) approved two types of vaccines: pneumococcal conjugate vaccine and pneumococcal polysaccharide vaccine (http://www.nlm.nih.gov/medlineplus/pneumococcalinfections.html). In Russian Federation following vaccines are approved: Pneumo 23 (PPSV23)—a 23-valent pneumococcal polysaccharide vaccine produced by Sanofi Pasteur, France and Prevenar™ (PCV7)—a 7-valent pneumococcal polysaccharide conjugate vaccine produced by Wyeth Pharmaceuticals Inc., USA.

The pneumococcal polysaccharide vaccine (PPSV) is indicated for adults. The majority of adults vaccinated with the PPSV develop resistance to the majority of bacterial strains (the antigens of which are present in the vaccine) 2-3 weeks after inoculation. Among elderly people, children under 2 years, and persons with chronic diseases, vaccination may not lead to generation of persistent immunity, or the immunity to the disease may not develop entirely (http://www.nlm.nih.gov/medlineplus/languages/pneumococcalinfections.html#Russian). Moreover, vaccination can cause such complications as erythema, algesthesis at the injection site, fever, myalgia or severe local reactions (Donalisio M R, Rodrigues S M, Mendes E T, Krutman M. Adverse events after pneumococcal vaccination. J Bras Pneumol. 2007 February; 33(1):51-6).

However, the PPSV turned to be significantly effective only among people with low risk for contracting pneumococcal disease. For children aged under 2 years, simultaneous prophylaxis with antibiotics use during the vaccination is recommended (Bacle A, Diot P, Lemarié E. Anti-pneumococcal vaccine: justifications and results. Rev Pneumol Clin. 1997; 53(3):128-37).

It appeared that the PPSV did not reduce frequency of pneumonia and its fatality rate, but only lowered risk for contracting severe pneumococcal infection. It was also shown that current vaccine did not protect from pneumococcus strains sensitive to penicillin at high concentrations (Pneumococcal vaccine: a second look. Solution for SC or IM injection: pneumococcal vaccine. Prescrire Int. 1998 February; 7(33):16-8). Such results were also reported for people aged over 65 years (Pneumococcal vaccination for elderly subjects: license extension. Still no proof of clinical efficacy. Prescrire Int. 2000 August; 9(48):106-9).

Active ingredient of the PPSV is a mixture of streptococcal polysaccharides of 23 serotypes, which cause up to 90% of invasive diseases with pneumococcal etiology. A polysaccharide is an antigen associated with the T-cell reaction, thus it leads to the development of the short-term immunization solely, without forming immune memory; vaccines containing only above-noted ingredients are ineffective, what has been shown for children aged under 2 years (Greenwood B M et al., Trans R Soc Trop Med Hyg, 1980, 74:756-760; publication of international application WO2010120921 A1, priority date 16 Apr. 2009). The fact that over 90 serotypes of pneumococci exist, as infectious agents of different areas of the world vary, also complicates producing of universal polysaccharide-based vaccine.

Along with polysaccharides of seven pneumococcal serovars, which most frequently cause diseases in children, a conjugate vaccine recommended for children, contains a carrier-protein CRM 197 (diphtheria toxin mutant), which fulfills the role of adjuvant. Due to the presence of adjuvant in the vaccine, this antigen complex is well recognized by T-cells assuring persistent immunity (Schneerson R, Barrera O, Sutton A, Robbins J B. Preparation, characterization, and immunogenicity of Haemophilus influenzae type b polysaccharide-protein conjugates. J Exp Med. 1980 August 1; 152(2):361-76). CRM 197 binds to heparin-binding EGF-like growth factor (HB-EGF). Despite the fact that the toxicity of CRM197 is approximately 106 times lower than that of diphtheria toxin, one should use it carefully, especially at high doses (Takuya Kageyama, Minako Ohishil, Shingo Miyamoto, Hiroto Mizushima, Ryo Iwamoto and Eisuke Mekada. Diphtheria Toxin Mutant CRM197 Possesses Weak EF2-ADP-ribosyl Activity that Potentiates its Anti-tumorigenic Activity. Received Apr. 16, 2007. Accepted May 2, 2007). Therewithal, vaccination can cause following complications: erythema, dermatodynia and induration at the injection site, rise in body temperature to 38-39° C. (100.4-102.2° F.) as well as restlessness, sleepiness and loss of appetite. Moreover, it is recommended to vaccinate children in the age of 2 years 4 times, in the age of 2 to 5 years—depending on the age of the child. In total, at least four doses are needed to vaccinate a child, which is expensive and unsafe.

A vaccine is known containing two main components: a superficial polysaccharide of N. meningitidi and a PsaA-protein of S. pneumoniae (PspA-protein can also be used) (publication of international application WO2010120921 A1, priority date 16 Apr. 2009). Taking into consideration the inability to develop immune memory to polysaccharides, we deem usage of the superficial polysaccharide of N. meningitidi as a vaccine component to be inappropriate. The usage of the PsaA- and PspA-proteins in its turn is reasonable: those are pneumococcal superficial antigens, which are capable of inducing both immune response and immune memory.

The effect of a vaccine to be patented is based on the induction of strong immune response and the subsequent development of the immune memory. Therefore the central position of our invention is occupied not by polysaccharides, but by pneumococcal proteins obtained using methods based on molecular biology and recombinant DNA. According to data in literature, the most promising protein-based antigens are three superficial proteins: PsaA, PspA, Spr1895.

PsaA-protein is also considered to be a promising immunogen by the authors of the international application publicized as WO2004102199 A2, priority date 16 May 2003. The authors mention this and several other proteins (SlrA—lipoprotein rotamase, IgA1—protease, PpmA—streptococcal maturation protein) or their compounds as the basis for the vaccine creation. However, we consider approach of using other surface proteins of S. pneumoniae—beside PsaA, PspA and Spr1895—to be more promising.

A chimeric protein containing PsaA and B subunit of cholera toxin with adjuvant function is described (Arêas A P, Oliveira M L, Miyaji E N, Leite L C, Aires K A, Dias W O, Ho P L. Expression and characterization of cholera toxin B-pneumococcal surface adhesin A fusion protein in Escherichia coli: ability of CTB-PsaA to induce humoral immune response in mice. Biochem Biophys Res Commun. 2004 Aug. 13; 321(1):192-6). However, we believe it is less safe to use cholera toxin or its compounds—compared to flagellin—as a vaccine component, whereas human organism is highly sensitive to cholera toxin, so that even 8 μg of toxin can cause strong diarrhea.

Studies have shown that it is reasonable to use PsaA- and PspA-proteins as basis for a pneumococcal vaccine creation. The PsaA-protein is highly conserved among different pneumococcal serotypes and provides bacterial adhesion and its virulence (Berry A M, and Paton J C: Sequence heterogeneity of PsaA, a 37-kilodalton putative adhesin essential for virulence of Streptococcus pneumoniae. Infect Immun 1996; 64:5255-5262). It was shown that PsaA specific antibodies possess a cross-linking activity towards all serotypes of S. pneumonia.

PspA is a choline-binding surface antigen that inhibits complement-independent phagocytosis, binds to lactoferrin, and prevents lactoferrin-independent elimination of bacterial cells (Hammerschmidt S, Bethe G, Remane P H, Chhatwal G S (1999) Identification of pneumococcal surface protein A as a lactoferrin-binding protein of Streptococcus pneumoniae. Infect Immun 67:1683-1687). In this paper the PsaA-protein is mentioned to be promising for producing of the vaccine. The authors have also shown a range of protein candidates for producing vaccines against pneumococcal infection; however, we consider it to be reasonable to use two particular proteins: PsaA and PspA, considering their conservatism among serotypes of pneumococci and several other bacteria.

One of the main components of the offered vaccine is a Spr1895-protein coded by the gene of a phosphate-binding protein—phosphate ABC transporter. This protein is essential for bacterial viability and constant, which makes it the component of choice for producing of the pneumococcal vaccine against S. pneumonia-caused diseases.

In the present invention, flagellin protein FliC fulfills function of adjuvant. Due to its interaction with Toll-like receptor-5 (TLR-5), FliC stimulates maturation of macrophages and dendritic cells, which results in development of the immune response (Mc Dermott P. F. High-affinity interaction between Gram-negative flagellin and a cell surface polypeptide results in human monocyte activation. Infect. Immun. —2000.—V. 68. —p.: 5525-5529; Means T. K. et al. The Toll-like receptor 5 stimulus bacterial flagellin induces maturation and chemokine production in human dendritic cells. J. Immunol.—2003.—V. 170. —p.: 5165-5175).

Currently, flagellin is considered to be one of the most promising and well characterized new generation adjuvants. The results of the research show that recombinant proteins injected together with flagellin possess increased immunogenic and antigenic characteristics. Reactions thereto are recorded in shorter terms and result in stronger cell-mediated and humoral immune response (Balaram, 2008).

In the present invention it is shown that flagellin components can function as adjuvant. Two receptor-activating domains were discovered in the terminal regions of flagellin (aa 79-117 and aa 408-439) (Tonyia, 2001).

Thus, the approach using definite components of flagellin is reasonable (FliC domain 1, FliC domain 2).

TLR-5 is expressed on the surface of the cells of the innate immunity, epithelial, and endothelial cells (Sebastiani G. et al. Cloning and characterization of the murine Toll-like receptor 5(Tlr5) gene: sequence and mRNA expression studies in Salmonella-susceptibleMOLF/Eimice. Genomics.—2000.—V. 64.—p.230-240; Zarember K. A. and Godowski P. J. Tissue expression of human Toll-like receptors and differential regulation of Toll-like receptor mRNAs in leukocytes in response to microbes, their products, and cytokines. J. Immunol.—2002.—V.168.—p.554-561; Delneste, 2007). In view of this, it is reasonable to use mucosa for immunization, which considerably facilitates transport of an immunogen.

In such a way, the invention described in WO2004102199 A2 and construct CTB-PsaA described in article mentioned above can be referred to to be the most akin to the present invention. However, in the mentioned international application it is proposed to use proteins or their functional units as separate vaccine components. Our invention is yet based on a chimeric protein that except for its specific S. pneumoniae protein constituent also includes an adjuvant. Therefore, the prototype of the present invention is a chimeric protein described by the Brazil authors.

The chimeric protein CTB-PsaA includes PsaA of the 6B serotype of S. pneumoniae (289 aa) as well as the B-subunit of cholera toxin functioning as adjuvant (Arêas A P, Oliveira M L, Miyaji E N, Leite L C, Aires K A, Dias W O, Ho P L. Expression and characterization of cholera toxin B-pneumococcal surface adhesin A fusion protein in Escherichia coli: ability of CTB-PsaA to induce humoral immune response in mice. Biochem Biophys Res Commun. 2004 August 13; 321 (1):192-6). However, it is more beneficial and easy—for provision of the correct molecular folding—to use a protein fragment, the antigenic determinant instead of the full-sized protein. Exactly this approach—usage of the most immunogenic protein fragments—was taken for creation of this invention. We do also consider usage of cholera toxin or its components as a vaccine component to be less safe in comparison to flagellin, since people are highly sensitive to the cholera toxin, and even 8 μg toxin can cause strong diarrhea. As for the method for producing of this chimeric protein, the gene encoding PsaA-protein was amplified separately from the plasmid, in which it was later inserted, followed by cloning via restriction-sites in a vector containing the CTB-encoding gene. In our case we used synthesis of the full-sized gene coding for the chimeric protein.

SUMMARY OF THE INVENTION

The present invention embodies a pneumococcal vaccine comprising a highly purified chimeric protein set forth as SEQ ID NO: 1 containing immunogenic fragments of *Streptococcus pneumoniae*, proteins PspA, Spr1895, PsaA [*Streptococcus pneumoniae*]), as well as flagellin components, connected via flexible links, wherein the flagellin components function as adjuvant. The fragment of PspA protein used is characterized by amino acids 160-262 of this protein, the sequence of which may be found, for example, by GenBank accession number EHD89266, version EHD89266.1. The fragment of Spr1895 protein used is characterized by amino acids 94-161 of this protein, the sequence of which may be found, for example, by GenBank accession number ZP 01836139, version ZP 01836139.1. The fragment of PsaA protein used is characterized by amino acids 238-309 of this protein, the sequence of which may be found, for example, by GenBank accession number AAF70667, version AAF70667.1. The fragments of flagellin used are characterized by amino acids 1-169 and 311-405, accordingly, of this protein, the sequence of which may be found, for example, by GenBank accession number AAB33952, version AAB33952.1. The vaccine according to the present invention is obtained as a result of mixing of the highly purified chimeric protein with a physiologically acceptable carrier.

For producing of the chimeric protein as consistent with the present invention, standard methods of molecular biology and biotechnology can be used, which are familiar to a person having ordinary skill in the art. Such methods are described in scientific literature in full measure.

Following the introduction of the vaccine, the organism produces antibodies against the epitopes of bacterial surface proteins present in the vaccinal chimeric protein and gains the ability to produce antibodies in response to the ingress of *S. pneumoniae*. Antigenic determinants of conservative pneumococcal proteins present in all serovars of the mentioned microbe are represented in the chimeric protein of the vaccine; thus the immune response after vaccination will be developed upon confrontation with every pneumococcal serovar. The usage of epitopes of several proteins will allow increasing of the vaccine efficacy. Presence of the protective antibodies against *S. pneumoniae* in human serum will allow a person not to sicken or to come through an illness better.

The vaccine possesses both preventive and therapeutic effects.

The technical result of the invention use is in universal defense from pneumococci due to the availability of both preventive and therapeutic effects in relation to diseases caused by *S. pneumoniae*, according to the fact that the protein is presented by immunogenic epitops of several conservative pneumococcal proteins on which specific immune response is released with immunological memory formation.

The technical result of the invention use is also in immune response strengthening to the vaccine active component due to adjuvant represented by flagellin components.

The technical result is also in vaccine safety increase according to the use of nontoxic agent—adjuvant represented by flagellin components.

DETAILED DESCRIPTION OF THE INVENTION

Examples

Example 1

Modeling of the Chimeric Protein

The planned chimeric polypeptide is a complex multidomain protein (5 domains: FliC1, FliC2, PspA, PsaA, Spr1895). For modeling of multidomain proteins following procedures were performed: estimation of the domain boarders, construction of a model of the full protein for estimation of the domain orientation, construction of models for each domain (using examples of 3D structures and ab initio-based modeling), docking of the models using the model of the full protein.

In the planned chimeric polypeptide two domains possessed prototypes and three thereof needed the ab initio-based modeling; furthermore during the ab initio-based modeling we had to form flexible links between domains.

For generation of the realistic results in automatic mode, an I-Tasser algorithm was used, which had been considered the best in the last three CASPs (Critical Assessment of protein Structure Prediction)—protein-modeling competitions. This analysis was being performed for three days. However, even by means of this strong algorithm, the generation of realistic data for the multidomain protein including the ab initio-based modeling of domains and their boarders is not fully valid (70%).

For the purpose of generation of more exact data, the protein was split into used domains, and then their modeling was performed using I-Tasser, followed by their docking.

Figure 1:
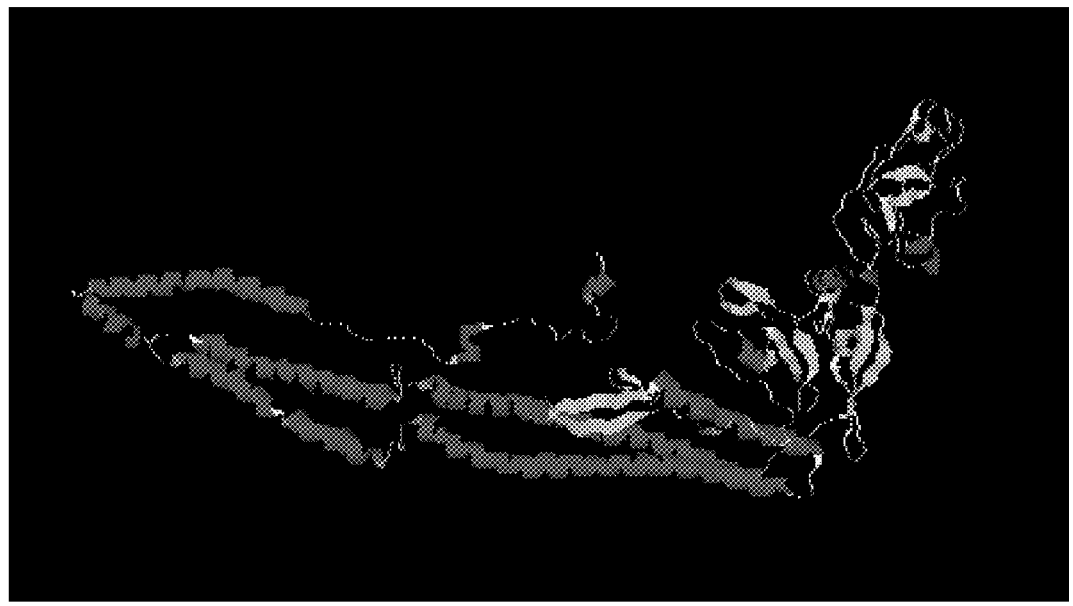
FIG. 1. 3D-structure of the chimeric protein, α-helices and β-sheets are depicted.
Figure 2:
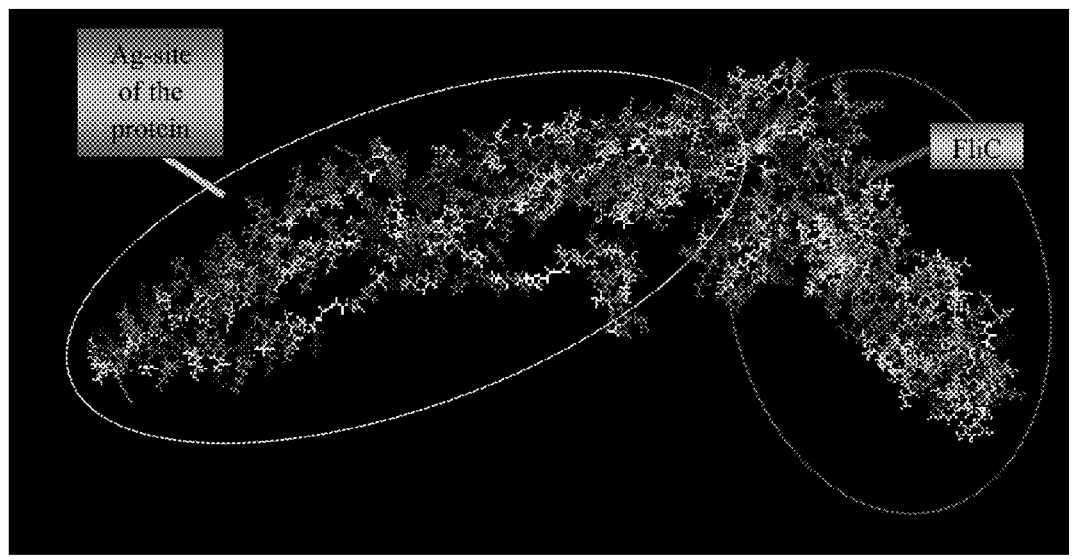
FIG. 2. 3D-structure of the chimeric protein, amino acid residues are depicted.

After all the steps mentioned above, the construction resulted, shown in FIGS. 1, 2.

The modeled chimeric protein consists of 536 amino acid residues; its amino acid sequence is given—SEQ ID NO:1. Analysis of the amino acid sequence of this protein via ProtParam program (http://au.expasy.org/tools/protparam.html) has shown that the molecular weight of the chimeric protein is 56.6 kDa, pI 4.56.

Example 2

Producing of Nucleotide Sequence Encoding the Chimeric Protein

The amino acid sequence of the chimeric protein containing fragments of PspA, Spr1895, PsaA, FliC was translated to the nucleotide sequence (1623 bp), which was then optimized for the expression in the *E. coli* cells.

Synthesis of this nucleotide sequence was performed via elongation of the overlapping oligonucleotides according to the described methods (Majumder, 1992). Oligonucleotides represented fragments of the chimeric gene being 70 nucleotides long, containing overlapping regions of 20 nucleotides. The main primer requirements were as follows: their length was not allowed to exceed 60 nucleotides, while the hybridization sites were not allowed to be shorter than 20 nucleotides. Furthermore, the long terminal G/C repeats were not allowed to exist. In certain cases selection of the optimal primers was performed empirically via primer-template movement or primer length changing by 3-6 nucleotides. Altogether for synthesis of the 1623 by long chimeric gene, 59 primers were used. Synthesized fragments (300 by each) were extracted via gel-electrophoresis and cloned into the plasmid vector pGEM-T Easy. The cloning was performed involving restriction sites Kpnl, SacII, EcoRV, BamHI or via blunt ends, as the case may be. After sequencing the fragments were amplified and then joined into a nucleotide sequence of the chimeric protein via polymerase chain reaction (PCR). After the final stage of the chimeric gene synthesis via ligation of the fragments, the artificial gene was cloned into the pGEM-T vector via KpnI and SacI restriction sites. The produced gene was flanked by additional restriction sites: EcoRI at the 5' end and XhoI at the 3' end. Next, the artificial gene was recloned into the expression vector pET24a via EcoRI and XhoI restriction sites.

Example 3

Producing of Plasmid DNA Encoding the Chimeric Protein

According to the methods described in the example 2, a nucleotide sequence for producing of the pneumococcal vaccine was obtained.

The resulting gene was cloned into the pET24a plasmid for the subsequent expression. Therefor ligation of the gene and the pET24a vector via appropriate buffer and ligase was performed. The reaction was being performed at +20° C. for 2 hours.

The mixture was being warmed up at +95° C. for 10 min, and then salts were removed via dialysis through nitrocellulose membrane filters with the pore size of 0.025 μm (Millipore, USA). The dialysis was being performed against the solution containing 0.5 mM EDTA in 10% glycerol for 10 min.

Example 4

Producing of *E. coli* Strain for Amplification of the Plasmid DNA Encoding Chimeric Gene According to the methods described in the example 3, a nucleotide sequence of the gene for creation of the pneumococcal vaccine was produced and cloned into the pET24a vector. The *E. coli* cells from the strain DH10B/R (Gibko BRL, США) possessing following genotype: F-mcrA Δ(mrr-hsdRMS-mcrBC) φ80dlacZΔM 15 ΔlacX74 deoR recAl endAl araD139 Δ(ara, leu)769 galU galKλ-rpsL nupG were transformed with the resulted plasmid via electroporation.

After the transformation, the cells were being incubated in SOC medium (2% bacto-tryptone, 0.5% yeast extract, 10 mM NaCl, 2.5 mM KCl, 10 mM $MgCl_2$, 10 mM $MgSO_4$, 20 mM glucose) for 40 min at +37° C.

Via screening of the *E. coli* cells for identification of the presence of the plasmid in the selective medium containing LB-agar and 100 μg/ml ampicillin, the appropriate *E. coli* cells were sampled to obtain the *E. coli* strain for the subsequent amplification of the plasmid DNA containing the chimeric gene.

The plasmid DNA was extracted from the grown clones with Wizard Minipreps DNA Purification System kit (Promega, USA) use.

The purified plasmid DNA was proven to be the needed one via restriction analysis and sequencing. In course of research, the clones were sampled, which contained DNA fragments of required size in the plasmids. Next, such plasmids were extracted for the subsequent induction of the gene expression.

Example 5

Obtaining of the *E. coli* Producer Strain of the Chimeric Protein

According to the methods described in the example 4, a nucleotide sequence of the protein was obtained for producing of the pneumococcal vaccine and then cloned into the pET24a plasmid; the resulted plasmid was amplified in the *E. coli* cells from the strain DH10B/R and then extracted.

For the expression of the protein, the *E. coli* cells from the strain BL21 Star (DE3) (Invitrogen, USA) with following genotype: F-ompT hsdSB (rB-mB-) gal dcm rne131 (DE3), containing λDe3 lysogen and rne131 mutation in genome were used. The mutant rne-gene (rne131) encodes the short version of RNase E that reduces intracellular mRNA degradation and in such a way increases its fermentative stability. The lon- and ompT-mutations in protease genes allow obtaining high yields of nonproteolysed recombinant proteins.

The *E. coli* cells from the strain BL 21 with genotype F-ompT hsdSB (rB-mB-) gal dcm rne131 (DE3) were prepared as following. The cells were being incubated at +37° C. overnight in 5 ml L-broth, containing 1% tryptone, 1% yeast extract and 1% sodium chloride. The culture was diluted 50-100-fold in fresh L-broth and was being cultivated in a shaking incubator at +37° C. until the optical density (OD) of 0.2-0.3 at 590 nm wave length. After having reached 0.3 OD, the culture was diluted in the fresh L-broth until 0.1 OD and was being cultivated for 30 min. The culture in the volume of 100 ml was transferred to a sterile centrifuge tube, and cell pelleting was being performed at +4° C., 5000 g for 10 min. The supernatant was discarded, and the cells were resuspended in deionized water to the initial volume under subsequent centrifuging. The washing steps were repeated three times. After washing, the cell pellet was resuspended in a small volume of deionized water and the suspension was being centrifuged for 30 sec at 5000 rpm in a microcentrifuge.

The transformation of the competent cells was performed via electroporation. Therefore 1 μl of plasmid DNA was added to 12 μl of competent cells, and the suspension was mixed. The subsequent electroporation was performed via pulse generator GVI-1 (ГВИ-1) (St. Petersburg State Polytechnical University, St. Petersburg) in sterile chambers at 10 kV/cm for 4 msec.

After transformation the cells were being incubated in SOC medium (2% bacto tryptone, 0.5% yeast extract, 10 mM NaCl, 2.5 mM KCl, 10 mM $MgCl_2$, 10 mM $MgSO_4$, 20 mM glucose) for 40 min at +37° C. 10-100 μl cell suspension was transferred to selective LB medium (Gibko BRL, USA) containing ampicillin (100 μg/ml) for selection of the clones with the plasmids (producer strains).

The plasmid obtained after transformation of the competent E. coli cells provides the high level of expression of the encoded recombinant protein.

Example 6

Producing of the Chimeric Protein for the Creation of the Pneumococcal Vaccine in E. coli Cells via Protein Synthesis Induction by 0.2% Lactose According to Studier Method According to the methods described in the example 5, the nucleotide sequence of the chimeric protein for the creation of the pneumococcal vaccine was obtained and cloned in the pET24a plasmid; the obtained plasmid was amplified in E. coli cells from the strain DH10B/R, extracted, and E. coli cells from the strain BL21 were transformed therewith for the purpose of induction of the target gene expression.

For the purpose of cultivation of the obtained producer strains, standard agarized LB medium containing ampicillin (100 μg/ml) and 1% glucose for blocking of nonspecific expression was used.

The expression induction was performed after the cell culture had reached the optical density of 0.6-0.8 OD at 600 nm. 0.2% lactose was used as inductor (Studier, 2005).

For autoinduction of the expression according to Studier's method (Studier, 2005), PYP-5052 medium was used containing 1% peptone (Gibco, USA), 0.5% yeast extract (Gibco, USA), 50 mM $Na_2HPO_4$, 50 mM $K_2HPO_4$, 25 mM $(NH_4)_2SO_4$, 2 mM $MgSO_4$, 0.5% glycerol, 0.05% glucose and 0.2% lactose.

A single producer strain colony was inoculated into PYP-5052 medium containing ampicillin (100 μg/ml). The fermentation was being performed at +37° C. in a thermostatic shaker at 250 rpm for 20 hours until no significant change in the $OD_{600}$ per hour was recorded. An aliquot of the cells was taken for the purpose of expression analysis of the gene encoding the vaccine protein. The expression analysis was performed via polyacrylamide gel electrophoresis (PAGE). The rest of the biomass was pelleted in the centrifuge at 9000 g.

The protein was extracted from the E. coli cells via cell lysis. The cells were resuspended in the lysis buffer containing 20 mM tris-HCl pH 7.5, 5 mM EDTA, and 1 mM Phenoxymethylsulfonylfluoride (PMSF), on 1 g cells per 5-7 ml buffer basis. The cell suspension was exposed to ultrasound 7 times for 30 sec at a 30 sec interval (22 kHz). The lysate was being centrifuged for 10 min at +4° C., 5000 g. The supernatant was discarded, and the pellet was resuspended in 1 M urea solution on 10 ml per 1 g cells basis by intensive mixing. The centrifuge step was repeated. The supernatant was discarded, and the pellet was resuspended in 2 M urea solution of the same volume. The centrifuge step was repeated. The supernatant was discarded.

According to the SDS-Page (Polyacrylamide Gel Electrophoresis with Sodium Dodecyl Sulfate) data, the obtained product contained approximately 97% of the chimeric protein, concentration 1 mg/ml.

The extraction and purification conditions were adjusted experimentally and can vary to some extent known to a person of ordinary skill in the art familiar with it.

Example 7

Protective Effect of the Vaccine Comprising the Chimeric Protein Containing Fragments of PspA, Spr1895, PsaA, FliC in the Prophylactic Model of Fatal Infection with S. pneumoniae For the estimation of the protective effect of the chimeric protein mice were used.

Figure 3:
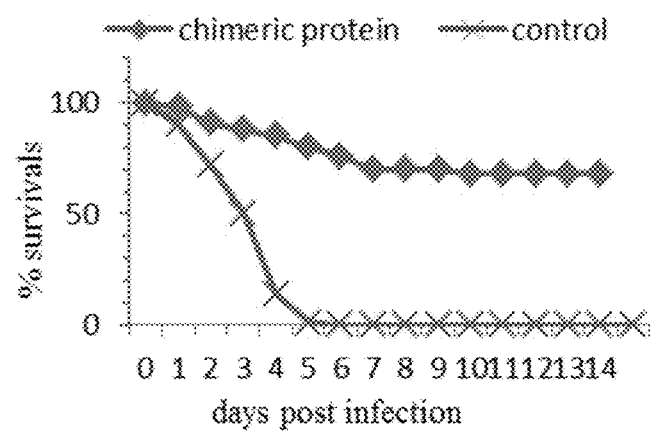
FIG. 3. Dynamics of mouse survival (%) after infection with 1 LD *S. pneumoniae* (prophylactic model).
Figure 4:
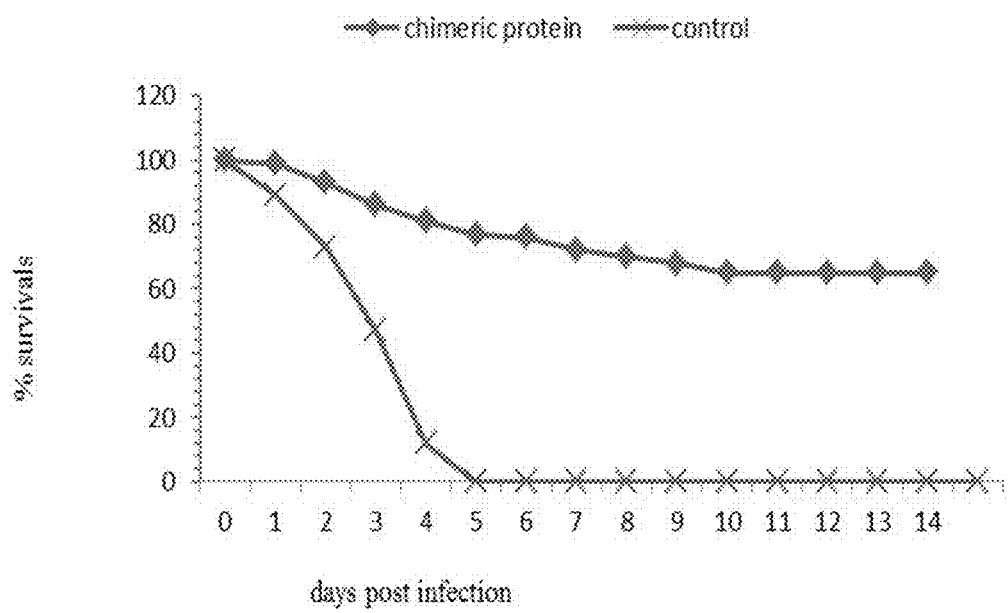
FIG. 4. Dynamics of mouse survival (%) after infection with 1 LD *S. pneumoniae* (therapeutic model).

The control and the experimental group consisted of 30 Balb/c female mice aged 7-8 weeks (18-20 g weight). 10 μg of chimeric protein were introduced in each mouse. One week after the inoculation, the mice were infected with pneumococci: $10^4$ cfu (colony-forming units) of S. pneumoniae per mouse were injected abdominally (this is the minimum lethal dose for a mouse). The survival study began immediately after the injection of the lethal dose of pneumococci and lasted for 14 days (FIG. 3).

The mice immunized with the recombinant chimeric protein-based vaccine showed the survival rate of 80% one week after infection and of 68% by day 14. The survival rate of the control group amounted 0% by day 5.

Thus, the offered vaccine possesses protectional effect. Moreover, the tested dose of the vaccine (10 μg/mouse) did not have any toxic effect on the mice.

Example 8

Protectional Effect of the Vaccine Comprising the Chimeric Protein Containing Fragments of PspA, Spr1895, PsaA, FliC in the Therapeutic Model of Fatal Infection with S. pneumoniae The control and the experimental group consisted of 30 Balb/c female mice aged 7-8 weeks (18-20 g weight). The mice were infected with pneumococci: $10^4$ cfu (colony-forming units) of S. pneumoniae per mouse were injected abdominally (this is the minimum lethal dose for a mouse). On the same day 10 μg of chimeric protein were inoculated in each mouse. The survival study began immediately after the injection of the lethal dose of pneumococci and lasted for 14 days.

After the simultaneous introduction of both pneumococci and the chimeric protein-based vaccine, the mice showed survival rates of 76% one week after introduction and 65% by day 14. The survival rate of the control group amounted 0% by day 5.

Such results prove high immunogenicity of the vaccine offered in the present invention. Thus, the vaccine can be used for the therapy of pneumococcal infections.

---

What is claimed is:

1. A pneumococcal vaccine comprising a chimeric protein set forth as SEQ ID NO: 1 containing fragments of *Streptococcus pneumoniae* proteins PspA, Spr1895 and, PsaA, as well as, flagellin components connected via flexible links, wherein the flagellin components function as adjuvant.

* * * * *